US010508386B2

(12) United States Patent
Udayakantha et al.

(10) Patent No.: US 10,508,386 B2
(45) Date of Patent: Dec. 17, 2019

(54) TEXTILE MATERIAL AND PROCESS FOR OBTAINING THE SAME

(71) Applicant: Sri Lanka Institute of Nanotechnology (Pvt) Ltd., Homagama (LK)

(72) Inventors: Krawe Sharini Malsha Udayakantha, Homagama (LK); Danushika Charyangi Manatunga, Homagama (LK); Kalu Marakkala Nalin de Silva, Homagama (LK); Gehan Anil Joseph Amaratunga, Homagama (LK)

(73) Assignee: Sri Lanka Institute of Nanotechnology (Pvt) Ltd., Homagama (LK)

( * ) Notice: Subject to any disclaimer, the term of this patent is extended or adjusted under 35 U.S.C. 154(b) by 688 days.

(21) Appl. No.: 15/141,301

(22) Filed: Apr. 28, 2016

(65) Prior Publication Data
US 2017/0314187 A1    Nov. 2, 2017

(51) Int. Cl.
*D06M 11/70* (2006.01)
*A01N 59/02* (2006.01)

(52) U.S. Cl.
CPC ........... *D06M 11/70* (2013.01); *A01N 59/02* (2013.01)

(58) Field of Classification Search
CPC ............................ D06M 11/70; A01N 59/02
USPC .......................................................... 442/131
See application file for complete search history.

(56) References Cited

U.S. PATENT DOCUMENTS

| | | | |
|---|---|---|---|
| 7,629,000 B2 | 12/2009 | Sebasan | |
| 7,855,161 B2 * | 12/2010 | Aso | A61L 9/18 423/610 |
| 2011/0232653 A1 * | 9/2011 | Imashiro | A41D 13/1192 128/863 |

FOREIGN PATENT DOCUMENTS

JP    H11256472    *    9/1999

OTHER PUBLICATIONS

Maleknia et al., Antibacterial Properties of Nanosized Silver Colloidal Solution on Wool Fabric, Asian Journal of Chemistry (2010), 22(8):5925-5929.
Shahidi et al., Antibacterial Agents in Textile Industry, Antimicrobial Agents, Chapter 19, Published: Sep. 12, 2012 under CC BY 3.0 license.
Wakamura, Photocatalysis by Calcium Hydroxyapatite Modified with Ti(IV), Fujitsu Sci. Tech. J. (Jul. 2005), 41 (2):181-190.

* cited by examiner

*Primary Examiner* — Cephia D Toomer
(74) *Attorney, Agent, or Firm* — Bret E. Field; Bozicevic, Field & Francis LLP (57) ABSTRACT

The present disclosure relates to modified textile material, wherein the modification is carried out by treating textile material with Hydroxyapatite. Such modified textile materials show bacterio-repulsion by preventing bacteria from attaching to their surfaces, thereby preventing malodor formation. The present disclosure also relates to process for obtaining the modified textile material as well as use of Hydroxyapatite as a bacterial repellent agent for preparing odor free textile material.

18 Claims, 6 Drawing Sheets

TEXTILE MATERIAL AND PROCESS FOR OBTAINING THE SAME

TECHNICAL FIELD

The present invention relates to the field of textile industry in general. Particularly, the present disclosure relates to textile material modified with Hydroxyapatite nanosol which imparts a bacterial repellence property to said textile material. The present disclosure also relates to process for obtaining the modified textile material as well as use of Hydroxyapatite as a bacterial repellent agent for preparing odor free textile material.

BACKGROUND

Polyester fabrics are ideal in active and sportswear mainly due to their high breathability which ensures the comfort of the wearer during heavy workout sessions. However, these fabrics are being greatly rejected from these communities irrespective of the comforting touch and feel, because of the strong malodor they produce upon standing even after a strong detergent wash. This malodor development is found to be related to the special surface make up of polyester fabrics.

A preliminary investigation on the structure reveals that polyester yarns have grooves on their surfaces as an inherent structural property unlike the case of nylon and cotton where the surface appears to be smoother with no grooves. The presence of grooves enhances wicking and drying properties of polyester fabrics which make them better candidates in sportswear surpassing common active wear yarns. Quick passage of water through polyester fabrics is ensured by its fibers being hydrophobic and hence not getting wet much. Presence of grooves on the fiber surface further enhances the breathability of polyester fabrics by empowering the capillary channel system through which water flows in the fabric by the capillary action.

Even though grooved surface is very advantageous in polyester, in turn it is also the biggest weakness of it. This is because, when the surface is filled with grooves, it provides a versatile breeding ground for the skin flora. Bacteria associated with skin flora get readily attached irreversibly to these hydrophobic surfaces through hydrophobic interactions. Once attached, they colonize forming a biofilm on the attached surface. In the process of their multiplication and growth, odorless apocrine secretions (rich in glutamine conjugates) are degraded to produce odorous compounds like short chain fatty acids (C6-C10): like pelargonic (C9) capric acid (C10) and 3-methyl-2-hexenoic acid (C7) being the most common. The formation of these odorous compounds make the polyester garments stink even after continuous laundering.

Human axilla is dominated by four major classes of bacteria which include staphylococci, aerobic coryneforms, propionibacteria and micrococci species that are responsible for the aforementioned biotransformation of odorless organic precursors to their respective odoriferous compounds. Polyester fabrics get susceptible to malodor development when these microbes in skin flora migrate onto the fabric and start degrading the sweat compounds adsorbed into fabrics during workouts. Grooves on polyester which are meant to be the elements for increasing drying and wicking properties of fabrics for the breeding ground for these microbes.

Therefore, development of odor free polyester fabric is marked as a compromise between maintaining the breathability of polyester while preventing the bacterial degradation of sweat compounds on them. There are a number of commercial products with embedded organic and inorganic bactericidal agents and nano silver, nano titania based surface finishes. See Shahidi, S., Wiener, J. (2012) Antibacteral Agents in Textile Industry, V. Bobbarala (Ed.), Antimicrobial Agents ISBN: 978-953-51-0723-1, InTech, DOI: 10.5772/46246, U.S. Pat. No. 7,629,000 B2, Maleknia, L., et al., Antibacterial properties of Nanosized Silver Colloidal Solution on Wool Fabric, Asian journal of Chemistry, 2010, 22(8), 5925-5929.

Photocatalysis by Calcium Hydroxyapatite Modified with Ti (IV), Masato Wakamura, Fujitsu Sci. Tech. J., 41, 2, p. 181-190, July 2005 discloses the photocatalysis activity of Hydroxyapatite Modified with Ti (IV). In the document, the author discloses that Ti (IV) modified Hydroxyapatite shows bactericidal activity.

However, all these finishes are antibacterial finishes. Even though they prevent the odor development of polyester, there's a risk of death of beneficial skin flora during their mechanism of action.

There is a need to develop modified fabrics, which while tackling the issue of odor development, would also not cause any detrimental effect on the skin flora whereby none of the beneficial microorganisms would be killed or their growth retarded as a result of such modification.

Thus, while in the prior art, agents used for coating textiles/fabrics are anti-bacterial agents which kill bacteria, the agent used for treating textile/fabric in the present invention functions by modifying the surface of the fabric/textile and acts as a bacterio-repulsive agent, thereby not causing any harm to the skin flora. These aspects are not known in the prior art.

SUMMARY OF THE INVENTION

Accordingly, the present invention relates to a modified textile material comprising textile material and Hydroxyapatite; a process for obtaining modified textile material, said process comprising acts of: (a) treating textile material with hydroxyapatite solution to obtain treated textile material and (b) curing the treated textile material to obtain the modified textile material; use of Hydroxyapatite as a bacterial repellent; and use of Hydroxyapatite for preparing odor free textile material selected from textile substrate, fabric or garment.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where.

DETAILED DESCRIPTION OF THE INVENTION

The present invention relates to a modified textile material comprising textile material and Hydroxyapatite.

In an embodiment of the present invention, the textile material is selected from textile substrate, fabric or garment; and wherein the textile material is composed of component selected from the group comprising polyester, wool, cotton, spandex, linen and acrylic, or any combinations thereof, preferably polyester.

In another embodiment of the present invention, the hydroxyapatite is coated on the textile material and is in sol form.

In yet another embodiment of the present invention, the hydroxyapatite is embedded into grooves of said textile material.

In still another embodiment of the present invention, the hydroxyapatite has particle size ranging from about 700 nm to about 2500 nm and nano spiky ends having width ranging from about 15 nm to about 30 nm; and wherein the ratio of the textile material to the Hydroxyapatite ranges from about 1:25 to about 1:70, preferably about 1:50.

The present invention also relates to a process for obtaining modified textile material, said process comprising acts of:
(a) treating textile material with hydroxyapatite solution to obtain treated textile material; and
(b) curing the treated textile material to obtain the modified textile material.

In an embodiment of the present invention, prior to the act of treating the textile material with the hydroxyapatite solution, the hydroxyapatite solution is prepared by hydrolysis of calcium salt and cationic dihydrogen phosphate, optionally along with their hydrated form in alkaline water and pre-heated at temperature ranging from about 55° C. to about 60° C., preferably about 60° C.; and wherein prior to pre-heating, the hydroxyapatite solution is optionally diluted.

In another embodiment of the present invention, the hydrolysis comprises acts of:
(a) adding about 20 ml to about 25 ml of ammonia solution dropwise to about 20 ml to about 25 ml of solution of the calcium salt and the cationic dihydrogen phosphate, optionally along with their hydrated form, under stirring at temperature ranging from about 80° C. to about 85° C., preferably about 85° C.; for time duration ranging from about 1 hour to about 2 hours, to obtain milky solution; and (b) stirring the milky solution for time period raging from about 0.5 hours to about 1 hour, preferably about 1 hour; at temperature ranging from about 80° C. to about 85° C., preferably about 85° C., to obtain the hydroxyapatite solution.

In yet another embodiment of the present invention, the calcium salt optionally along with its hydrated form is selected from calcium chloride and calcium nitrate tetrahydrate.

In yet another embodiment of the present invention, the cationic dihydrogen phosphate, optionally along with its hydrated form is selected from sodium dihydrogen phosphate dihydrate and ammonium dihydrogen phosphate.

In yet another embodiment of the present invention, the textile material is selected from textile substrate, fabric or garment; and the textile material is composed of component selected from the group comprising polyester, wool, cotton, spandex, linen and acrylic, or any combinations thereof, preferably polyester.

In yet another embodiment of the present invention, the hydroxyapatite has particle size ranging from about 700 nm to about 2500 nm and nano spiky ends having width ranging from about 15 nm to about 30 nm; and wherein ratio of the textile material to the hydroxyapatite solution ranges from about 1:25 to about 1:70, preferably about 1:50.

In yet another embodiment of the present invention, treating of the textile material with the hydroxyapatite solution comprises act selected from dipping and dyeing, or a combination thereof, preferably dipping; and wherein the treating results in coating of the hydroxyapatite on the textile material; and wherein the treating is carried out at temperature ranging from about 55° C. to about 60° C., preferably about 60° C.; for time period ranging from about 45 minutes to about 1 hour, preferably about 1 hour.

In yet another embodiment of the present invention, the curing is carried out for time duration ranging from about 30 minutes to about 1 hour, preferably about 1 hour; at temperature ranging from about 105° C. to about 110° C., preferably about 110° C.

In yet another embodiment of the present invention, the modified textile material is processed to obtain garment.

In still another embodiment of the present invention, the textile material selected from textile substrate, fabric or garment thereof, is bacterial repellent and odor free.

The present invention further relates to use of Hydroxyapatite as a bacterial repellent.

In an embodiment of the present invention, the hydroxyapatite has particle size ranging from about 700 nm to about 2500 nm and nano spiky ends having width ranging from about 15 nm to about 30 nm.

The present disclosure further relates to use of Hydroxyapatite for preparing odor free textile material selected from textile substrate, fabric or garment.

In an embodiment of the present invention, the hydroxyapatite has particle size ranging from about 700 nm to about 2500 nm and nano spiky ends having width ranging from about 15 nm to about 30 nm.

To overcome the non-limiting drawbacks as stated in the background, the present invention relates to textile material, specifically modified textile material, and processes thereof.

In a non-limiting embodiment, the textile material is a textile substrate, fabric or garment and is composed of components selected from the group comprising polyester, wool, cotton, spandex, linen and acrylic or combinations thereof, preferably polyester.

In an embodiment, the textile material is surface modified to obtain the modified textile material.

In an exemplary embodiment, the modification is carried out by treating said textile material selected from textile substrate, fabric or garment with Hydroxyapatite (HAP).

In an embodiment of the present invention, the treating of the textile material results in coating or the distribution of Hydroxyapatite on the surface of the textile material as a uniform surface coating, covering all the fibres of the textile material.

In a non-limiting embodiment, the Hydroxyapatite is in nanosol form, having particle size ranging from about 700 nm to about 2500 nm with an average size of about 1774 nm. Additionally, the Hydroxyapatite sol comprises nano spiky ends having width ranging from about 15 nm to about 30 nm, with an average width of about 15 nm. Further, the ratio of textile material to Hydroxyapatite nanosol ranges from about 1:25 to about 1:70, preferably about 1:50.

In another embodiment, coating of the textile material selected from textile substrate, fabric or garment with Hydroxyapatite causes a change in the surface structure of the textile material such that bacterial adhesion is not favoured. Particularly, a coating of HAP on the textile material modifies the material surface, by embedding/filling up the grooves on the textile material so as to make it groove free, thus refining the irregularity and making the material smooth and appear and behave nylon like. Additionally, HAP has a total negative charge on its surface under neutral pH conditions, thereby repelling bacteria by electrostatic repulsion (Bacterial cell wall has a total negative charge which makes it attracted towards electropositive surfaces). Therefore, since bacteria can no longer attach to the modified surfaces of the textile material of the present invention, no degradation of odor free apocrine secretions to their respective odoriferous compounds occurs. This is especially useful in the case of polyester fabrics, which due to the presence of grooves on the surface, function as breeding grounds for skin flora, thus producing malodor. Further, breathability of the modified textile materials is improved and maintained at the expected levels. Particularly, high drying and wicking rates are maintained over continuous laundering up to 30 standard washing cycles.

The present invention relates to a process for obtaining the modified textile material selected from textile substrate, fabric or garment, wherein the textile material is surface modified to obtain the modified textile material.

In an embodiment, the textile material is surface modified by treating the textile material with Hydroxyapatite, followed by curing; and the modified textile material is optionally processed to obtain finished garment by conventionally known industrial methods.

In non-limiting embodiments of the present invention, the textile material may already be in the form of a garment before being treated with the Hydroxyapatite. The garment, treated with Hydroxyapatite is odor free after repeated launderings due to its bacteriorepulsive nature.

In an embodiment, the hydroxyapatite solution is prepared by hydrolysis of calcium salt and cationic dihydrogen phosphate, optionally along with their hydrated form in alkaline water. In this procedure, about 20 ml to about 25 ml of about 25% to about 30% ammonia solution is added to about 20 ml to about 25 ml of aqueous solution of the calcium salt and the cationic dihydrogen phosphate, optionally along with their hydrated form, under stirring for about 1 hour to about 2 hours to obtain a milky solution which is further stirred to obtain the hydroxyapatite solution. The hydroxyapatite solution is then pre-heated before treating the textile material. In non-limiting embodiments, prior to pre-heating, the hydroxyapatite solution is optionally diluted.

In another embodiment, the ammonia solution is added in a dropwise manner in order to obtain hydroxyapatite having particle size ranging from about 700 nm to about 2500 nm, with an average size of about 1774 nm. Particularly, dropwise addition of ammonia prevents the formation of a 'large number of small nuclei' which occurs when the addition is in bulk and quick which in turns gives rise to a mass of smaller sized particles. In order to prevent the same, in the present invention, the ammonia solution is added in a dropwise manner.

In another embodiment, the temperature at which the ammonia solution, the calcium salt and the cationic dihydrogen phosphate are stirred to obtain the milky solution ranges from about 80° C. to about 85° C., preferably at about 85° C. Thereafter, the milky solution is stirred for time period raging from about 0.5 hours to about 1 hour, preferably about 1 hour; at temperature ranging from about 80° C. to about 85° C., preferably about 85° C., to obtain the hydroxyapatite solution.

In an embodiment, the calcium salt optionally along with its hydrated form is selected from calcium chloride and calcium nitrate tetrahydrate. The cationic dihydrogen phosphate, optionally along with its hydrated form is selected from sodium dihydrogen phosphate dihydrate and ammonium dihydrogen phosphate.

In another embodiment, the hydroxyapatite solution is pre-heated to a temperature ranging from about 55° C. to about 60° C., preferably about 60° C. Additionally, in embodiments where the hydroxyapatite solution is diluted, the dilution is carried out with water at a volume dilution of up to 75. In a non-limiting embodiment, the dilution is carried out with water at a volume dilution of about 25.

In another embodiment, the textile material is treated with the hydroxyapatite by techniques such as dipping and dyeing, preferably dipping, or a combination of said techniques. Said treatment is carried out at temperature ranging from about 55° C. to about 60° C., preferably about 60° C., for time period ranging from about 45 minutes to about 1 hour, preferably about 1 hour. Additionally, the wet pick up is maintained at about 80%.

In another embodiment, post treatment, the treated material is cured at temperature ranging from about 105° C. to about 110° C., preferably about 110° C. for time period ranging from about 30 minutes to about 1 hour, preferably about 1 hour.

In an embodiment, the curing process promotes thermal diffusion of the HAP into the textile material, thereby producing a bacterial repellent/bacterio-repulsive finish on the textile material which is durable to laundering.

In another embodiment, the modified textile material thus obtained is optionally processed to obtain garment.

The present invention also relates to use of hydroxyapatite as a bacterial repellent/bacterio-repulsive agent as well as its use for preparing odor free textile material.

Additional embodiments and features of the present invention will be apparent to one of ordinary skill in the art based upon the description provided herein. The embodiments herein provide various features and advantageous details thereof in the description. Descriptions of well-known/conventional methods and techniques are omitted so as to not unnecessarily obscure the embodiments herein. Further, the invention herein provides for examples illustrating the above described embodiments, and in order to illustrate the embodiments of the present invention, certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1: Preparation of Hydroxyapatite Sol (HAP)

Example 1.1

Hydroxyapatite sol is prepared by the hydrolysis of Calcium nitrate tetrahydrate and ammonium dihydrogen phosphate in alkaline water. In this procedure, about 25 ml of 25% ammonia solution is added dropwise to about 25 ml of an aqueous solution of Calcium nitrate tetrahydrate and ammonium dihydrogen phosphate, under vigorous stirring at about 85° C. A milky solution is obtained and the mixture is stirred for about 1 hour at about 85° C. to obtain Hydroxyapatite sol.

Example 1.2

Hydroxyapatite sol is prepared by the hydrolysis of Calcium chloride and ammonium dihydrogen phosphate in alkaline water. In this procedure, about 25 ml of 25% ammonia solution is added dropwise to about 25 ml of an aqueous solution of Calcium chloride and ammonium dihydrogen phosphate, under vigorous stirring at about 85° C. A milky solution is obtained and the mixture is stirred for about 1 hour at about 85° C. to obtain Hydroxyapatite sol.

Example 1.3

Figure 1:
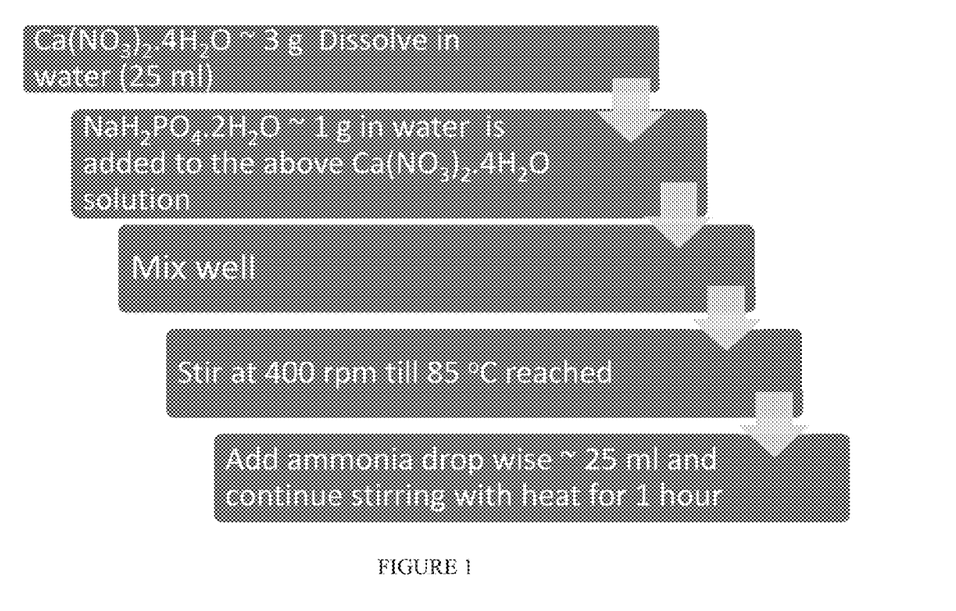
FIG. 1 is a flowchart depicting an exemplary process for the synthesis of HAP according to an embodiment.

Hydroxyapatite sol is prepared by the hydrolysis of Calcium nitrate tetrahydrate and Sodium dihydrogen phosphate dihydrate in alkaline water. In this procedure, about 25 ml of 25% ammonia solution is added dropwise to about 25 ml of an aqueous solution of Calcium nitrate tetrahydrate and Sodium dihydrogen phosphate dihydrate, under vigorous stirring (400 rpm) at about 85° C. A milky solution is obtained and the mixture is stirred for about 1 hour at about 85° C. to obtain Hydroxyapatite sol. (FIG. 1)

Example 1.4

Hydroxyapatite sol is prepared by the hydrolysis of Calcium chloride and Sodium dihydrogen phosphate dihydrate in alkaline water. In this procedure, about 25 ml of 25% ammonia solution is added dropwise to about 25 ml of an aqueous solution of Calcium chloride and Sodium dihydrogen phosphate dihydrate, under vigorous stirring at about 85° C. A milky solution is obtained and the mixture is stirred for about 1 hour at about 85° C.

Example 2: Material Characterization

Particle Size Analysis

Figure 3:
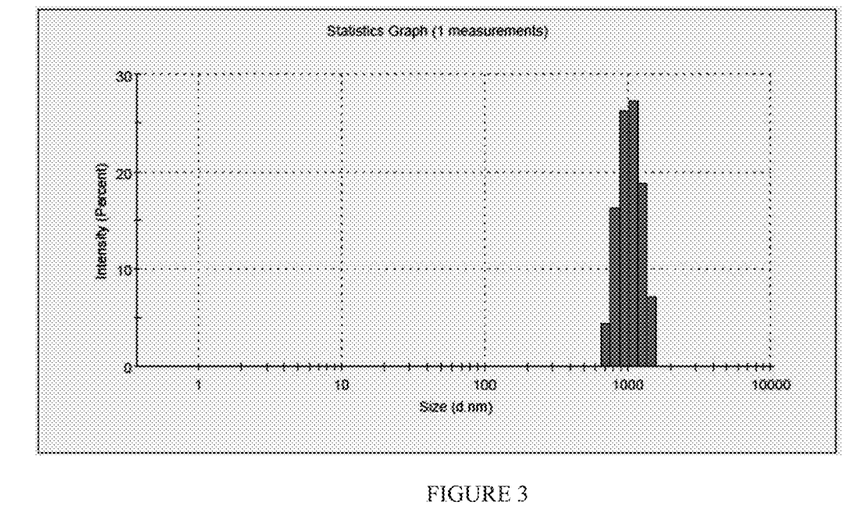
FIG. 3 is a histogram depicting the particle size of HAP according to an embodiment.

Particle size analysis is carried out for the HAP sol prepared as per Example 1 (1.1-1.4). FIG. 3 depicts the size statistics report for the HAP sample, showing the number intensities under different particle sizes. As can be observed from the histogram, HAP's size ranges from 700-2500 nm having an average size of 1774 nm.

Figure 4:
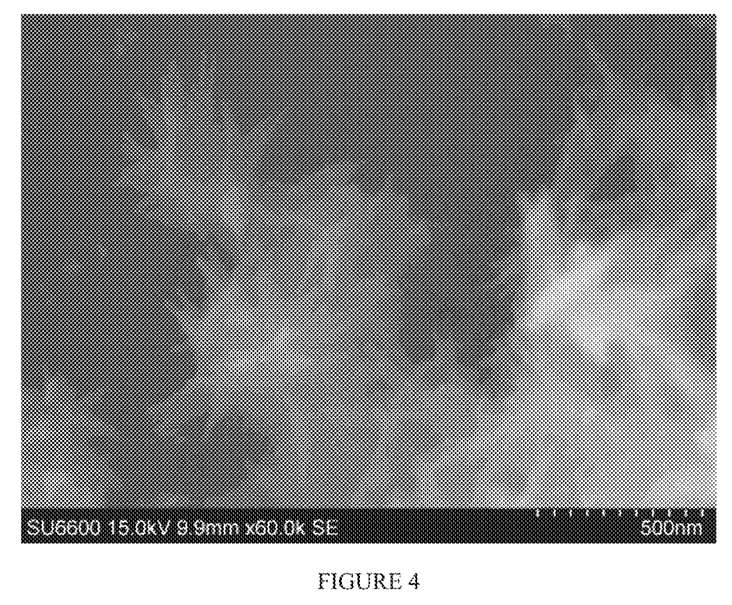
FIG. 4 depicts scanning electron micrograph of HAP used for fabric coating according to an embodiment.

Further, scanning electron micrograph of HAP as depicted in FIG. 4 reveals that HAP sol consists of micro size aggregates with a nano texture. The surfaces of these aggregates carry rod shaped spiky ends which are of nano scale aspect ratio.

Example-3: Fabric Treatment

With Undiluted HAP (HAP 0)—

Figure 2:
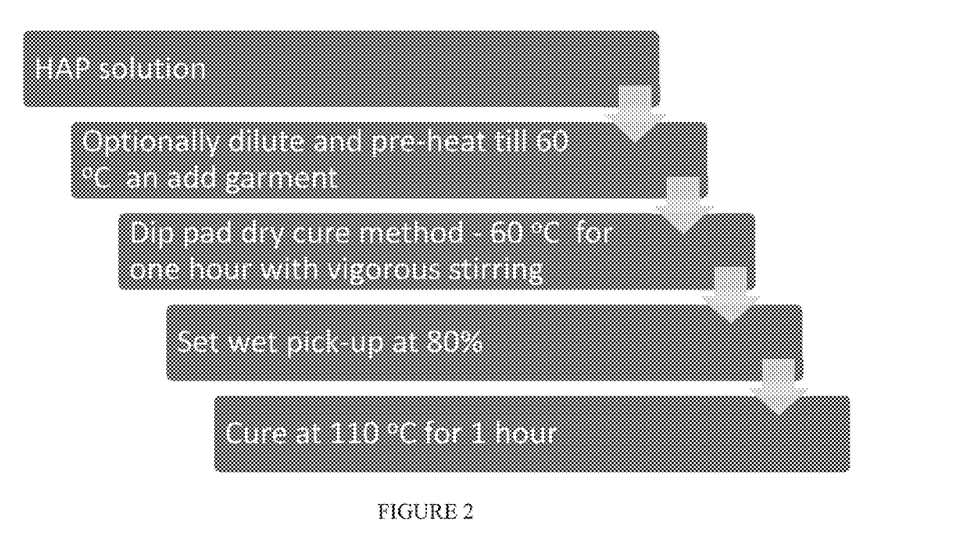
FIG. 2 is a flowchart depicting the process of treating fabric with HAP sol according to an embodiment.

The solutions prepared in example 1 (1.1-1.4) are pre-heated to a temperature of about 60° C. Polyester fabric is then dipped in any of the aforementioned solutions (with a fabric to solution ratio of 1:50) for about 1 hour at about 60° C. Wet pick up is maintained at about 80%. The treated samples are then cured at about 110° C. for about 1 hour. (FIG. 2).

With Diluted HAP (HAP 25)—

The solutions prepared in example (1.1-1.4) are diluted with water at a volume dilution factor of about 25. The solutions are then pre-heated to a temperature of about 60° C. Polyester fabric is then dipped in any of the aforementioned diluted solutions (with a fabric to solution ratio of 1:50) for about 1 hour at about 60° C. Wet pick up is maintained at about 80%. The treated samples are then cured at about 110° C. for about 1 hour. (FIG. 2).

Figure 5:
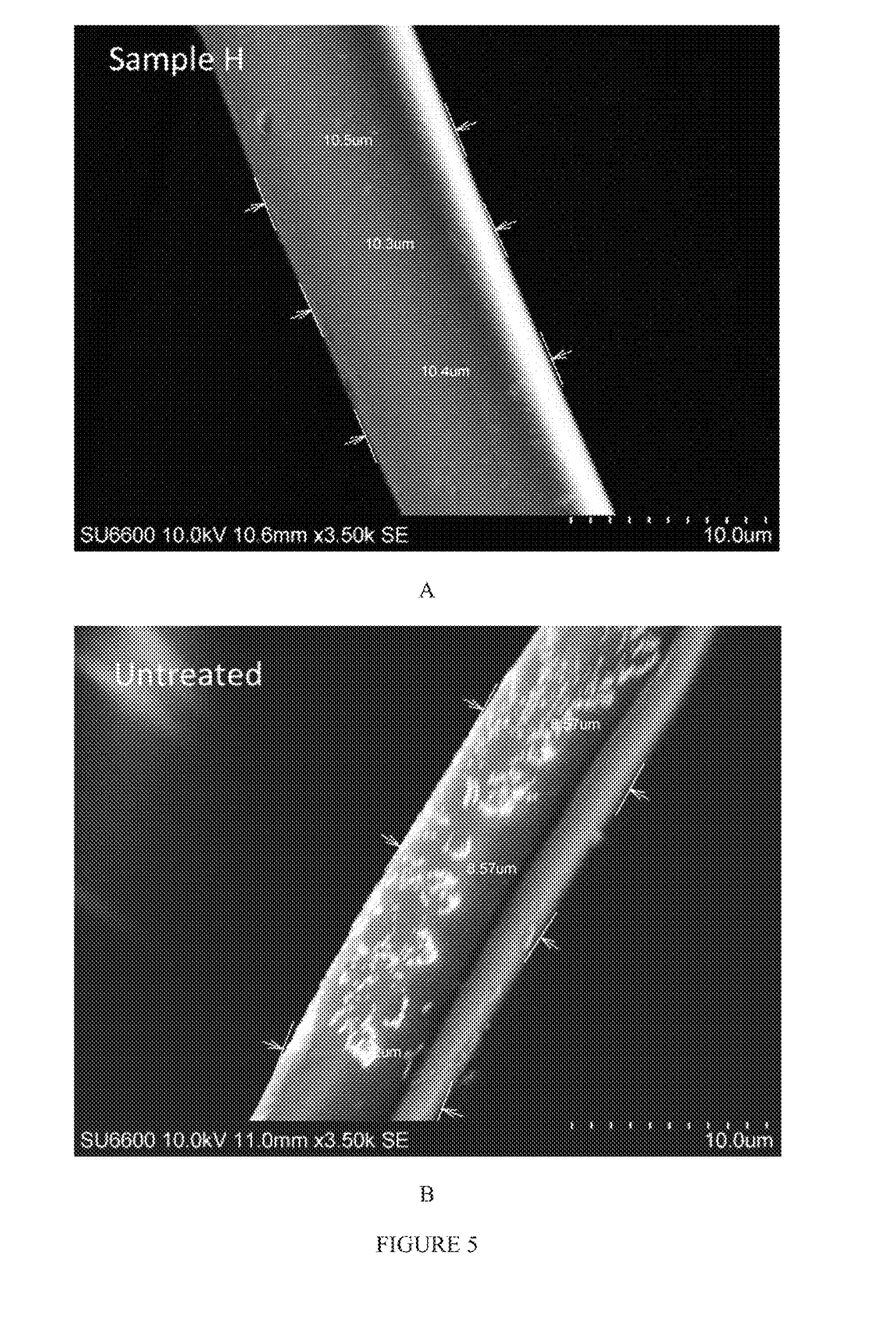
FIG. 5 depicts Higher Magnification scanning electron micrographs of HAP coated polyester (A) and untreated polyester (B) according to an embodiment.
Figure 6:
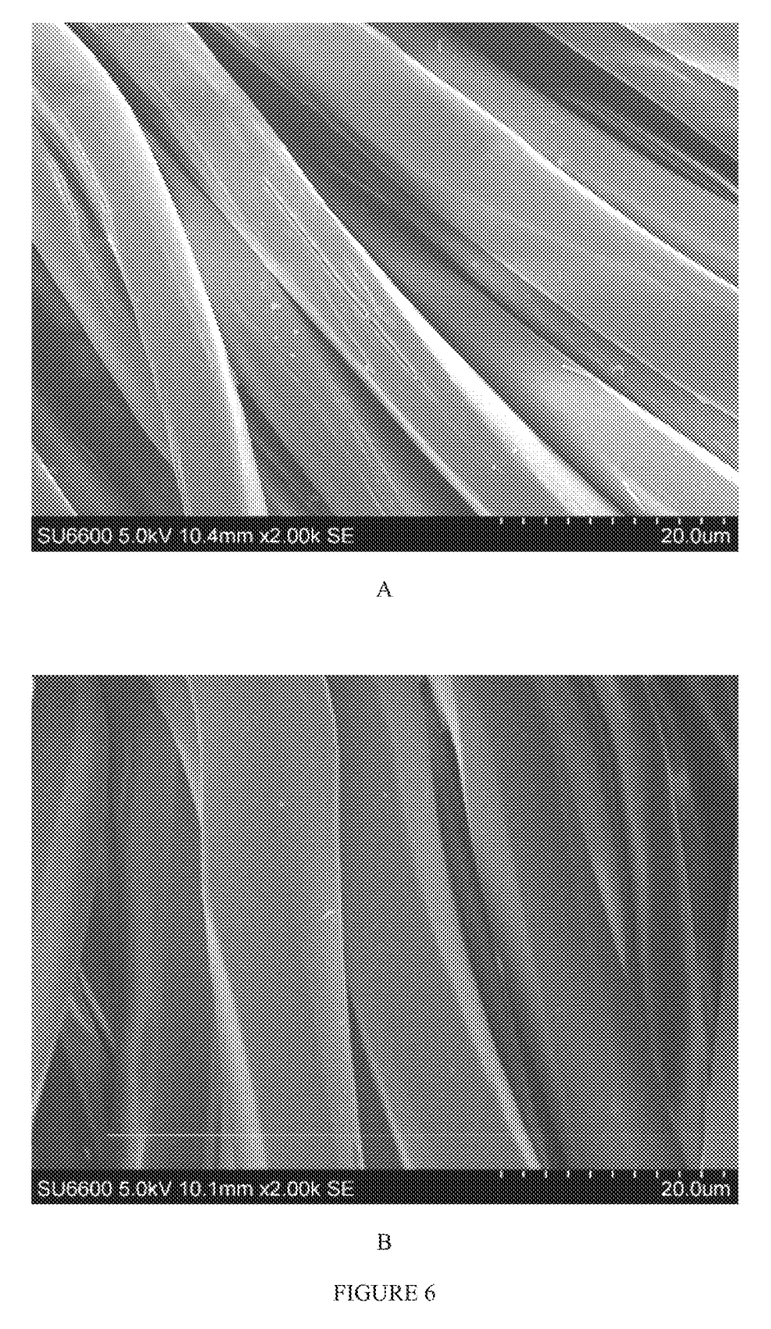
FIG. 6 depicts Lower Magnification scanning electron micrographs of untreated polyester (A) and HAP coated polyester (B) according to an embodiment.

FIGS. 5 and 6 depict the Higher Magnification and Lower Magnification Scanning Electron Micrographs of HAP coated polyester and untreated polyester, respectively. The Scanning Electron Micrographs show the fiber level appearance of Untreated and HAP coated polyester. It is evident from the figures that the untreated polyester fiber surface is full of grooves and hence is seldom smooth which is then converted into a smooth surface by the application of HAP as a top coat. As can be observed, the surface of the HAP coated polyester is free of grooves and hence bacterial adhesion is not facilitated.

Example-4: Testing for Bacteriorepulsive Activity

Figure 7:
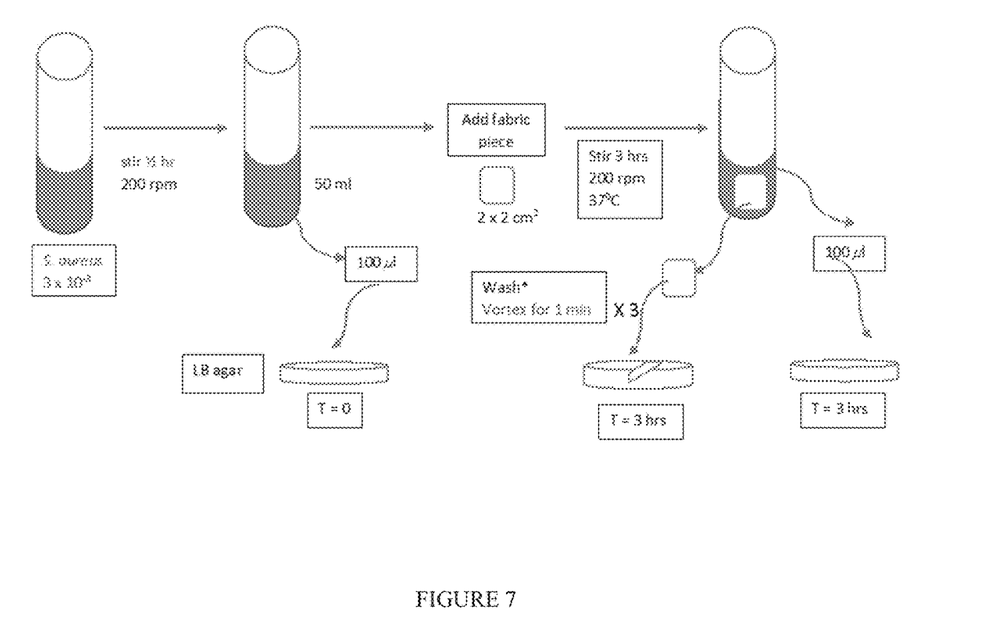
FIG. 7 depicts the standard operating procedure for the bacteriostasis testing of textile fabrics according to an embodiment.

A bacterial cell suspension (*S. aureus*) of known strength ($\sim 3 \times 10^3$ Colony Forming Units (CFU)) is prepared in autoclaved (about 120° C., about 20 minutes) distilled water and is shaken for about half an hour at about 200 rpm at about 37° C. or vortexed for not less than 15 minutes, preferably for about 20 minutes. A swatch of about 2 cm×2 cm fabric is cut from each fabric sample (autoclaved) and is added to the bacterial suspension (about 50 ml) at about 37° C. The suspensions are shaken at about 200 rpm for about 3 hours at about 37° C. Each fabric swatch is dipped, vortexed and vigorously shaken manually in an autoclaved screw capped vial with about 50 ml of autoclaved distilled water for about 1 minute (FIG. 7).

Spread Plating

Spread plating comprises the following steps:
- t=0—a 100 μl aliquot of the bacterial suspension is drawn before the addition of fabric swatches and spread plate is poured.
- t=3 hrs—a 100 μl aliquot of the bacterial suspension is drawn after about 3 hrs stirring and spread plate is poured.
- The washed fabric piece is cultured on an agar plate.
- Each test trial is accompanied by,
- a control sample; where no fabric piece is added before stirring.
- test sample; H (Diluted HAP treated polyester).

a reference sample; U (Untreated polyester)—handled the same way as treated fabrics.

Evaluation

Evaluation is carried out based on the following:

Same CFU count on both t=0 and t=3 hrs or the same pattern in CFU as seen for control sample, indicates the fabric is bacterio-repulsive A significant difference in two counts or change of pattern as seen for control sample, suggests otherwise.

No colony growth on or around the fabric piece confirms fabric's bacteria repellency.

Comment

In a condition where a total bacterial repellency is demonstrated, bacterial colony counts in t=0 and t=3 of the treated sample should be similar to the pattern shown by the control sample, along with zero bacterial growth on or around the test fabrics.

Test Results

TABLE 1

Test Results of Bacterio-repulsive Activity

| Sample | Replicate | T = 0 | T = 3 | Fabric Swatch |
|---|---|---|---|---|
| Control | 1 | $1.99 \times 10^3$ | $2.0 \times 10^3$ | Not Applicable |
|  | 2 | $2.00 \times 10^3$ | $2.0 \times 10^3$ |  |
| Untreated Polyester | 1 | $2.00 \times 10^3$ | $2.4 \times 10^3$ | Microbial growth is observed on fabric swatch and around the margins of fabric swatch |
|  | 2 | $1.98 \times 10^3$ | $2.5 \times 10^3$ |  |
| HAP25 treated Polyester | 1 | $1.99 \times 10^3$ | $1.90 \times 10^3$ | Microbial growth is not observed on fabric swatch and around the margins of fabric swatch |
|  | 2 | $1.98 \times 10^3$ | $1.89 \times 10^3$ |  |

Figure 8:
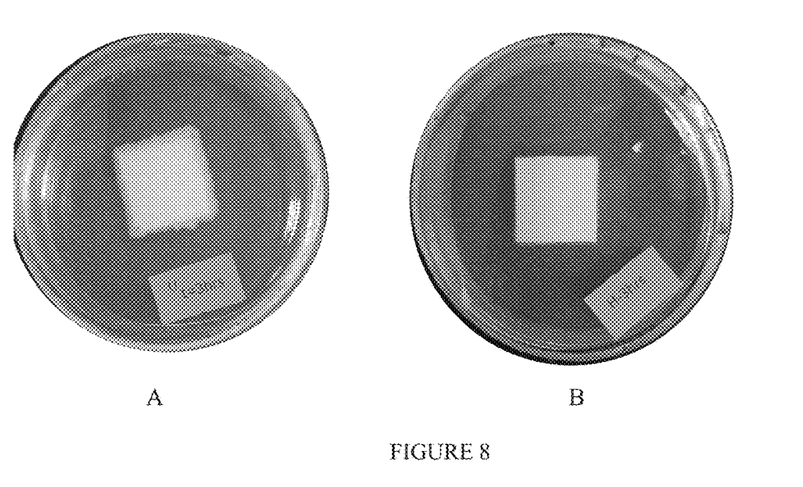
FIG. 8 depicts the tested fabric specimens after incubation at 37° C. according to an embodiment, wherein 'A' depicts the Untreated Polyester and 'B' depicts the HAP treated Polyester.

As shown in the above table, all bacterial colony counts are maintained in $10^3$ scale over the studied 3 hours' time and no microbial growth is seen on the HAP treated fabric though it is seen on and around the untreated polyester fabric (FIG. 8). This demonstrates the bacteria repellent property of HAP. However, the untreated polyester fabrics allow the increased growth and colonization of bacteria on the fabric.

Example-5: Antibacterial Activity Testing

Methodology

Antibacterial activity testing is carried out as per ISO 20743:2007.

Test fabrics treated with undiluted HAP as well as test fabrics treated with diluted HAP, each of about 0.4 g are cut and sterilized by autoclaving at temperature of about 121° C. for about 15 minutes. These are inoculated with the bacterial strains with an initial strength of about $10^5$ CFU/ml. The samples are then incubated at about 37° C. for about 24 hours and are washed with saline water. The amount of bacteria recovered into saline water after about 24 hours is counted and the percentage reduction of bacteria is calculated and reported as antibacterial activity value: A.

Test Parameters

Test parameters are provided below:
Sterilization Method: Autoclave At 121° C. for about 15 minutes
Neutralizing Solution: Letheen Broth
Incubation Temperature: About 37° C.
Contact Period: About 24 hours Test Culture: *Staphylocccus Aureus* (ATCC 6538) (Concentration Of Inoculum: $2.6 \times 10^5$ CFU/mL)

*Klebsiella Pneumoniae* (ATCC 4352) (Concentration Of Inoculum: $2.3 \times 10^5$ CFU/mL)

Test Specimen: About 0.4 g of Submitted Sample

Evaluation

A result yielding an A value equal or greater than 2 is regarded as representative for an antibacterial fabric finish.

Reference Rating:

| Efficacy of antibacterial property | Antibacterial Activity Value, A |
|---|---|
| Significant | $2 \leq A < 3$ |
| Strong | $A \geq 3$ |

Results

TABLE 2

Test Results of Antibacterial Activity

| | Antibacterial Activity Value | | |
|---|---|---|---|
| Test Microorganism | Untreated Polyester | HAP Treated Polyester (HAP 25) | HAP Treated Polyester (HAP 0) |
| *Staphylococcus aureus* | 0 | 1.0 | 0.3 |
| *Klebsiella pneumoniae* | 0 | 0 | 0 |

The collective result of bacteriorepulsive analysis and ISO standard reveals that there's no attachment of bacteria on the fabrics treated with diluted and undiluted HAP and that effect is not related to any killing of bacteria. Hence, these results validate that HAP particles treated polyester is a good bacteria repellent surface which is non-antibacterial/bactericidal.

Example-6: Test Method and Testing Procedure for Drying Time Assessment

Figure 9:
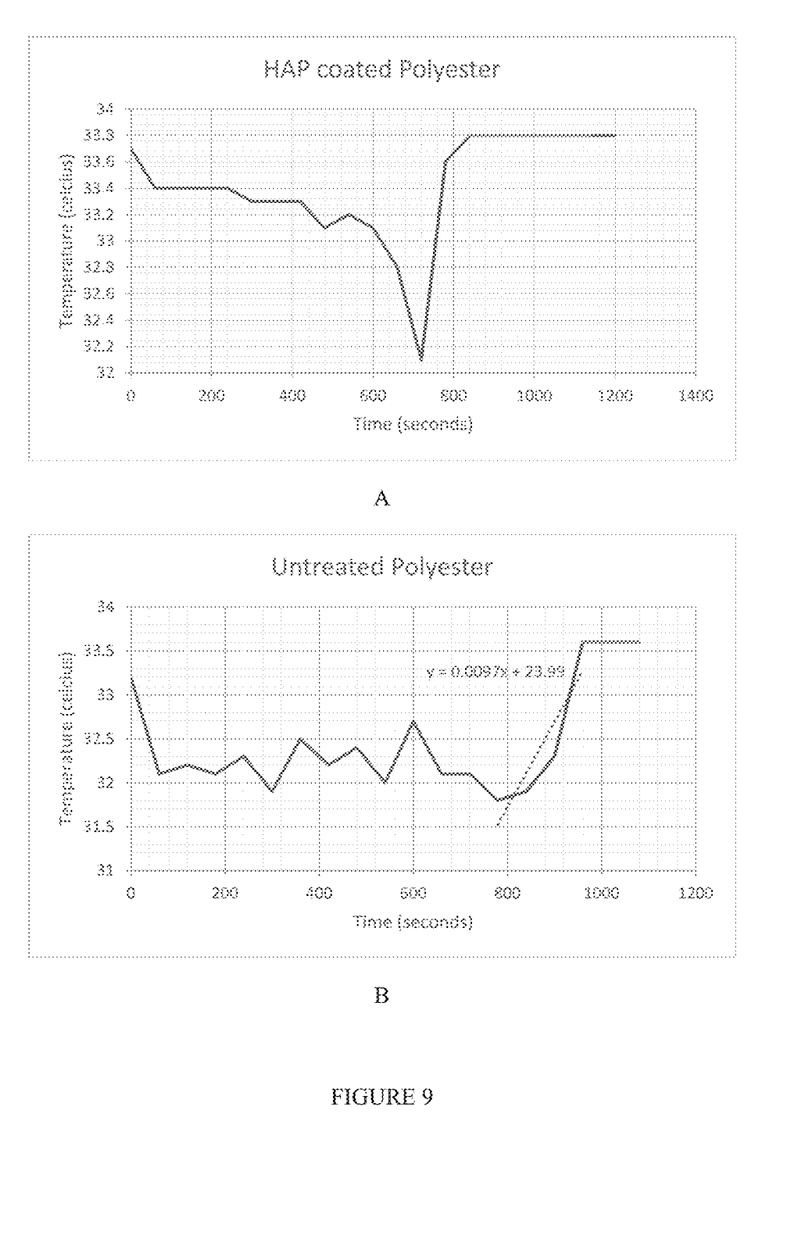
FIG. 9 is a graph depicting the drying time results, wherein surface temperature of the fabric over its wetted area is monitored as a function of time for HAP coated polyester (9A) and untreated polyester (9B).

NIKE Dry time test standard operating procedure NAL.SOP.5110.v1.0 is adopted for the testing. A hot plate is conditioned at about 37° C. for about 20 minutes prior to the testing. An aliquot of about 0.200 ml of water is pipetted on to the hot plate and placed in the centre of the hot plate. A fabric piece of interest (about 20 cm×20 cm) is placed on the hot plate covering the previously placed water drop (the fabric is positioned in a manner so as to get its centre wet by water). Surface temperature of the fabric over its wetted area is monitored as a function of time. Results are plotted (Temperature Vs Time) (FIG. 9) and the drying time (min) and drying rate (ml/hr) is calculated. Drying time is the time at which the temperature increases steeply and comes to a constant level in the graph provided in FIG. 9. Drying rate is calculated by dividing the volume of water used (0.2 ml) with the drying time. Results of treated fabrics are compared with the untreated fabrics.

TABLE 3

Results of drying time test

| Test Specimen | Drying time (minutes) | Drying Rate (ml/hr) |
|---|---|---|
| Untreated Polyester | 16.34 | 0.733 |
| HAP treated polyester (HAP 0) | 13.13 | 0.940 |

As can be observed in table 3 above, the treated fabric system shows drying rate superior to the untreated polyester.

Further, table 4 below shows the drying time results of HAP treated polyester up to 30 laundering cycles.

TABLE 4

Drying time Results of HAP treated Polyester

| Washes | HAP treated polyester (HAP 0) | |
|---|---|---|
| | Min | Rate (g/hr) |
| Unwashed | 13.13 | 0.914 |
| 5 Washes | 13 | 0.923 |
| 10 Washes | 13 | 0.923 |
| 15 Washes | 13.1 | 0.916 |
| 20 Washes | 13 | 0.923 |
| 25 Washes | 17.2 | 0.697 |
| 30 Washes | 21.95 | 0.546 |

As can be observed from the table above, HAP treated polyester shows high drying rates up to 30 washes. Although the drying rate of the HAP treated polyester decreases after 25 washes, it is still within the acceptable range.

Example-7: Test Method and Testing Procedure for Wicking Time Assessment

Vertical wicking NIKE apparel test method is adopted to assess wicking. Fabric strips of about 2.5 cm×20 cm size are cut from treated and untreated samples. Cut pieces are hung on a water filled measuring cylinder allowing only about 1 mm height of the fabric to get dipped in water. The travel length of water on the fabric strip is measured and expressed as the rate of travel (cm/5 min).

TABLE 5

Results of Vertical wicking test

| Test specimen | Wicking rate (cm/5 min) |
|---|---|
| Untreated polyester | 10.0 |
| HAP treated polyester (HAP 0) | 8.4 |

As can be observed from table 5 above, although the wicking rate of HAP treated polyester is less than the untreated one, it is still in the acceptable range with regard to NIKE standards on vertical wicking (>7.5 cm/5 min).

Further, table 6 below shows the wicking test results of HAP treated polyester up to 30 laundering cycles.

TABLE 6

Wicking Test Results of HAP treated Polyester

| Washes | HAP treated Polyester (HAP 0) Rate (cm/5 min) |
|---|---|
| Unwashed | 8.4 |
| 5 Washes | 9.3 |
| 10 Washes | 9.4 |
| 15 Washes | 9.4 |
| 20 Washes | 9.5 |
| 25 Washes | 10.0 |
| 30 Washes | 10.2 |

As can be observed from the above table, HAP treated polyester shows high wicking rates up to 30 wash cycles. In fact, the wicking rate of HAP treated polyester after 20 wash cycles is comparable to the wicking rate of untreated polyester.

Therefore it is evident that the present invention is able to successfully overcome the various deficiencies of prior art and provide for modified textile materials which due to HAP coating, reduce odor development with continuous laundering by functioning as bacterial repellents while maintaining the characteristic high breathability of the polyester intact. Further, the HAP used for coating the textile material is not bactericidal in nature as a result of which use of the modified textile material of the present invention does not cause harm to the useful skin flora.

Additional embodiments and features of the present invention will be apparent to one of ordinary skill in art based on the description provided herein. The embodiments herein provide various features and advantageous details thereof in the description. Descriptions of well-known/conventional methods and techniques are omitted so as to not unnecessarily obscure the embodiments herein.

The foregoing description of the specific embodiments fully reveals the general nature of the embodiments herein that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments in this invention have been described in terms of preferred embodiments, those of skill in the art will recognize that the embodiments herein can be practiced with modifications within the spirit and scope of the embodiments described herein.

Throughout the specification, the word "comprise", or variations such as "comprises" or "comprising" wherever used, will be understood to imply the inclusion of a stated element, integer or step, or group of elements, integers or steps, but not the exclusion of any other element, integer or step, or group of elements, integers or steps.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation. It is further understood that the scope of the present invention fully encompasses other embodiments that may become obvious to those skilled in the art and that the scope of the present invention is accordingly limited by nothing other than the appended claims.

We claim:

1. A modified textile material consisting of textile material and Hydroxyapatite, wherein the Hydroxyapatite is coated on the textile material and is in sol form.

2. The modified textile material as claimed in claim 1, wherein the textile material is selected from textile substrate, fabric or garment; and wherein the textile material comprises a component selected from the group comprising polyester, wool, cotton, spandex, linen and acrylic, or any combinations thereof.

3. The modified textile material as claimed in claim 1, wherein the hydroxyapatite is embedded into grooves of said textile material.

4. The modified textile material as claimed in claim 1, wherein the hydroxyapatite has particle size ranging from about 700 nm to about 2500 nm and nano spiky ends having width ranging from about 15 nm to about 30 nm; and wherein the ratio of the textile material to the Hydroxyapatite ranges from about 1:25 to about 1:70.

5. A process for obtaining the modified textile material as claimed in claim 1, said process comprising acts of:
   a) coating a textile material with a hydroxyapatite sol to obtain a coated textile material; and
   b) curing the coated textile material to obtain the modified textile material.

6. The process as claimed in claim 5, wherein prior to the act of coating the textile material with the hydroxyapatite sol, the hydroxyapatite sol is prepared by hydrolysis of calcium salt and cationic dihydrogen phosphate, optionally along with their hydrated form in alkaline water and pre-heated at temperature ranging from about 55° C. to about 60° C.; and wherein prior to pre-heating, the hydroxyapatite sol is optionally diluted.

7. The process as claimed in claim 6, wherein the hydrolysis comprises acts of:
   a) adding about 20 ml to about 25 ml of ammonia solution dropwise to about 20 ml to about 25 ml solution of the calcium salt and the cationic dihydrogen phosphate, optionally along with their hydrated form, under stirring at temperature ranging from about 80° C. to about 85° C.; for time duration ranging from about 1 hour to about 2 hours, to obtain milky solution; and
   b) stirring the milky solution for time period raging from about 0.5 hours to about 1 hour, preferably about 1 hour; at temperature ranging from about 80° C. to about 85° C. to obtain the hydroxyapatite sol.

8. The process as claimed in claim 7, wherein the calcium salt optionally along with its hydrated form is selected from calcium chloride and calcium nitrate tetrahydrate.

9. The process as claimed in claim 7, wherein the cationic dihydrogen phosphate, optionally along with its hydrated form is selected from sodium dihydrogen phosphate dihydrate and ammonium dihydrogen phosphate.

10. The process as claimed in claim 5, wherein the textile material is selected from textile substrate, fabric or garment; and the textile material is composed of component selected from the group comprising polyester, wool, cotton, spandex, linen and acrylic, or any combinations thereof.

11. The process as claimed in claim 5, wherein the hydroxyapatite has particle size ranging from about 700 nm to about 2500 nm and nano spiky ends having width ranging from about 15 nm to about 30 nm; and wherein ratio of the textile material to the hydroxyapatite sol ranges from about 1:25 to about 1:70.

12. The process as claimed in claim 5, wherein coating of the textile material with the hydroxyapatite sol comprises an act selected from dipping and dyeing, or a combination thereof; and wherein the coating is carried out at temperature ranging from about 55° C. to about 60° C.; for time period ranging from about 45 minutes to about 1 hour, preferably about 1 hour.

13. The process as claimed in claim 5, wherein the curing is carried out for time duration ranging from about 30 minutes to about 1 hour; at temperature ranging from about 105° C. to about 110° C.

14. The process as claimed in claim 5, wherein the modified textile material is processed to obtain a garment.

15. The modified textile material as claimed in claim 1, wherein the modified textile is a material selected from textile substrate, fabric or garment thereof, and is bacterial repellent and odor free.

16. The modified textile material as claimed in claim 2, wherein the textile material is polyester.

17. The modified textile material as claimed in claim 4, wherein the ratio of the textile material to the Hydroxyapatite is about 1:50.

18. The modified textile material as claimed in claim 1, wherein the modified textile material does not cause harm to skin flora.

* * * * *